US012736515B2

(12) United States Patent
Driscoll-Natale

(10) Patent No.: US 12,736,515 B2
(45) Date of Patent: Sep. 15, 2026

(54) H2O MONITORING FOR ALL

(71) Applicant: Jack Driscoll-Natale, Aptos, CA (US)

(72) Inventor: Jack Driscoll-Natale, Aptos, CA (US)

( * ) Notice: Subject to any disclaimer, the term of this patent is extended or adjusted under 35 U.S.C. 154(b) by 280 days.

(21) Appl. No.: 18/395,250

(22) Filed: Dec. 22, 2023

(65) Prior Publication Data

US 2025/0208110 A1 Jun. 26, 2025

(51) Int. Cl.
*G01N 33/18* (2006.01)

(52) U.S. Cl.
CPC ................................ *G01N 33/1886* (2013.01)

(58) Field of Classification Search
None
See application file for complete search history.

(56) References Cited

U.S. PATENT DOCUMENTS 6,677,861 B1 * 1/2004 Henry .................. E21B 47/017 370/254
2007/0050157 A1 * 3/2007 Kahn ..................... C02F 1/008 702/55
2007/0219728 A1 * 9/2007 Papageorgiou ....... G06T 11/206 702/23
2018/0160649 A1 * 6/2018 Hicks .................... A01K 29/00

FOREIGN PATENT DOCUMENTS

WO WO-2023158489 A1 * 8/2023 ......... G01N 33/1886

* cited by examiner

*Primary Examiner* — Eric S. McCall
*Assistant Examiner* — Nigel H Plumb
(74) *Attorney, Agent, or Firm* — Wilmer Cutler Pickering Hale and Dorr LLP

(57) ABSTRACT

Techniques for acquiring and publishing water quality data in real time are disclosed. In some embodiments, the techniques can be realized as a water quality monitoring device that can include a temperature sensor configured to acquire temperature data from a body of water, a potential of hydrogen (pH) sensor configured to acquire pH data from the body of water, and an oxidation-reduction potential (ORP) sensor configured to acquire the ORP data from the body of water.

20 Claims, 11 Drawing Sheets

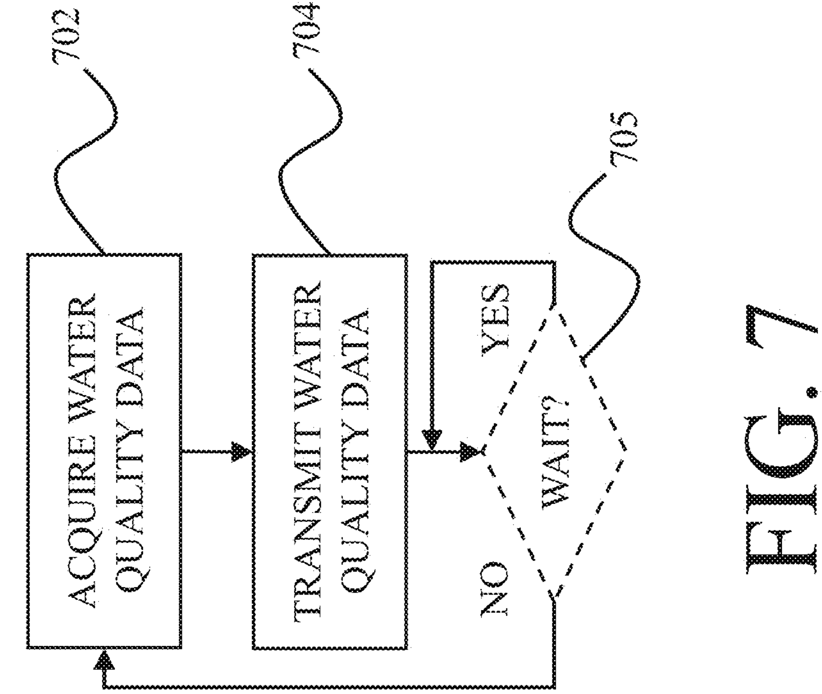
FIG. 7
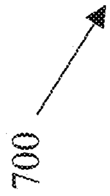

H2O MONITORING FOR ALL

FIELD OF THE DISCLOSURE

The present disclosure relates generally to monitoring water quality, and more particularly, to techniques for acquiring and disseminating water quality data.

BACKGROUND OF THE DISCLOSURE

As aquatic ecosystems continue to transform in response to climate change and other environmental threats, it is crucial that communities have extensive, updated information on the health of their natural water resources to guide environmental policy, conservation, and advocacy.

The field of water quality monitoring presents particular challenges. For example, current solutions to monitoring the quality of bodies of water do not report sensor data at a continuous or sufficiently frequent rate, are prohibitively expensive for levels of sensor accuracy comparable to data acquired by government environmental agencies, and are not user-friendly. Because water quality data is infrequently reported to publicly accessible sources on the Internet such as government environmental agency websites, communities lack an up-to-date awareness of bodies of water they may drink from, bathe in, or otherwise interact with. Even if people are motivated enough to go out and obtain the water quality data themselves, they face further obstacles. For example, some devices used to acquire water quality data of sufficient accuracy are so expensive that only large-scale laboratories and organizations can afford them, leaving no affordable and accessible option for the average citizen concerned about the health of their nearby bodies of water. Should a person have the means to afford one of these devices, the operation of such devices often requires substantial training or time investment to learn how to use them in the first place.

To overcome the challenges in providing communities with extensive, updated information on the health of their natural water resources, it would be useful to provide a water quality monitoring device that provides water quality data to the public that is updated on a continuous or regular basis, is accurate yet affordable, and is easy to deploy in the field yet resilient to the elements, such that its effectiveness scales with the number of such devices working together.

Current solutions to water quality monitoring are inadequate. Despite government environmental agencies establishing public databases of water quality data, such as the Water Quality Portal (WQP) provided by the United States Environmental Protection Agency (EPA), there are still significant deficits both in terms of geographical coverage as well as frequency of updates. Thus, what is needed is a solution to these long felt but unsolved needs.

SUMMARY OF THE DISCLOSURE

Techniques for acquiring and publishing water quality data in an efficient and cost-effective manner are disclosed.

In some embodiments, the techniques may be realized as a water quality monitoring device that includes a plurality of sensors configured to acquire water quality data from a sample of a body of water, the water quality data including temperature data, pH data, and ORP data. The plurality of sensors can include a temperature sensor configured to acquire the temperature data from the body of water, a potential of hydrogen (pH) sensor configured to acquire the pH data from the body of water, and an oxidation-reduction potential (ORP) sensor configured to acquire the ORP data from the body of water. A transceiver can be included in the device to wirelessly transmit the water quality data over a communication channel to a server. In addition, a memory storing program instructions and one or more processors can be included. The one or more processors can be configured to execute the program instructions stored in the memory to operate the plurality of sensors to generate the temperature data, the pH data, and the ORP data of the water quality data and operate the transceiver to wirelessly transmit the water quality data. The device can also include a power source configured to provide power to the plurality of sensors, the transceiver, the memory, and the one or more processors, and a housing containing the memory, the transceiver, the memory, the one or more processors, and the power source.

In accordance with other aspects of some embodiments, the plurality of sensors can consist of the temperature sensor, the pH sensor, and the ORP sensor.

In accordance with further aspects of some embodiments, the memory can be configured not to store the water quality data.

In accordance with additional aspects of some embodiments, the device can be configured to acquire and wirelessly transmit the water quality data in real time.

In accordance with other aspects of some embodiments, the one or more processors can be further configured to operate the plurality of sensors to generate additional water quality data every 10 seconds, the additional water quality data including additional temperature data, additional pH data, and additional ORP data acquired from an additional sample of the body of water, and operate the transceiver to immediately transmit the additional water quality data in response to the plurality of sensors generating the additional water quality data.

In accordance with further aspects of some embodiments, the one or more processors can be further configured to generate an alert responsive to determining the temperature data includes a temperature value that exceeds a predetermined range of temperature values, the pH data includes a pH value that exceeds a predetermined range of pH values, and/or the ORP data includes an ORP value that exceeds a predetermined range of ORP values.

In accordance with additional aspects of some embodiments, the one or more processors can be further configured to operate the transceiver to wirelessly receive additional water quality data from a separate water quality monitor device configured to acquire the additional water quality data from the body of water, combine the water quality data with the additional water quality data, and operate the transceiver to transmit the combined water quality data over the communication channel to the server.

In accordance with other aspects of some embodiments, the device can include a renewable power generator coupled to the water quality monitoring device and configured to provide renewable power to the power source. The renewable power generator can include one or more photovoltaic panels, one or more wind turbines, and/or one or more hydroelectric generators.

In accordance with further aspects of some embodiments, the transceiver can be configured to communicate using a Wi-Fi communication protocol.

In accordance with additional aspects of some embodiments, at least two of the water quality monitoring device can be included in a water monitoring system. The at least two of the water quality monitoring device can include a first water quality monitoring device and a second water quality monitoring device. The first water quality monitoring device can be configured to acquire first water quality data from a first location in the body of water and transmit the first water quality data over the communication channel to the server. The second water quality monitoring device can be configured to acquire second water quality data from a second location in the body of water and transmit the second water quality data over the communication channel to the server.

In accordance with other aspects of some embodiments, the temperature data, the pH data, and the ORP data can be acquired simultaneously from the body of water.

In accordance with further aspects of some embodiments, the one or more processors can be configured to calibrate each sensor of the plurality of sensors based on a regression analysis, a 1-point calibration method, or a 2-point calibration method.

In accordance with additional aspects of some embodiments, the one or more processors can be configured to operate the transceiver to wirelessly transmit the water quality data according to a timing schedule.

In accordance with other aspects of some embodiments, the timing schedule can be one transmission of the water quality data every n seconds, where n is an integer.

In accordance with further aspects of some embodiments, the timing schedule can be based on an amount of available power from the power source.

In some embodiments, the techniques can be realized as a water quality monitoring device that can include a transceiver and a plurality of sensors configured to acquire water quality data from a sample of a body of water, the water quality data including temperature data, pH data, and ORP data. The plurality of sensors can include a temperature sensor configured to acquire the temperature data from the body of water, a potential of hydrogen (pH) sensor configured to acquire the pH data from the body of water, and an oxidation-reduction potential (ORP) sensor configured to acquire the ORP data from the body of water. In addition, a memory storing program instructions and one or more processors can be included in the water quality monitoring device. The one or more processors can be configured to execute the program instructions stored in the memory to operate the plurality of sensors to generate the temperature data, the pH data, and the ORP data of the water quality data, operate the transceiver to wirelessly communicate with an external device using a wireless protocol.

In accordance with other aspects of some embodiments, the water quality monitoring device can be a first water quality monitoring device configured to communicate with a second water quality monitoring device including a second plurality of sensors.

In accordance with additional aspects of some embodiments, the external device can be the second water quality monitoring device.

In accordance with further aspects of some embodiments, the external device can be a smartphone, a wireless router, or a cellular base station.

In accordance with other aspects of some embodiments, the transceiver can be one of a Wi-Fi module and a cellular modem.

In some embodiments, the techniques can be realized as a method of monitoring a body of water, where the method can include providing a water quality monitoring device. The water quality monitoring device can include a plurality of sensors including a temperature sensor, a potential of hydrogen (pH) sensor, and an oxidation-reduction potential (ORP) sensor. The water quality monitoring device can also include a transceiver, a memory storing program instructions, one or more processors configured to execute the program instructions stored in the memory, a power source, and a housing containing the transceiver, the memory, the one or more processors, and the power source. The method can include establishing, by the one or more processors, a communication channel between the transceiver and a server, submerging the temperature sensor, the pH sensor, and the ORP sensor into the body of water, and operating, by the one or more processors, the plurality of sensors to acquire water quality data from a sample of the body of water, the water quality data including temperature data acquired with the temperature sensor, pH data acquired with the pH sensor, and ORP data acquired with the ORP sensor. The method can also include operating, by the one or more processors, the transceiver to wirelessly transmit the water quality data over the communication channel to the server.

In accordance with other aspects of some embodiments, providing the plurality of sensors can consist of providing the temperature sensor, providing the pH sensor, and providing the ORP sensor.

In accordance with further aspects of some embodiments, the memory can be programmed not to store the water quality data.

In accordance with additional aspects of some embodiments, the method can include acquiring and wirelessly transmitting the water quality data in real time.

In accordance with other aspects of some embodiments, the method can include generating additional water quality data every 10 seconds, the additional water quality data including additional temperature data, additional pH data, and additional ORP data acquired from an additional sample of the body of water, and immediately transmitting the additional water quality data in response to the plurality of sensors generating the additional water quality data.

In accordance with further aspects of some embodiments, the method can include generating an alert responsive to determining the temperature data includes a temperature value that exceeds a predetermined range of temperature values, the pH data includes a pH value that exceeds a predetermined range of pH values, and/or the ORP data includes an ORP value that exceeds a predetermined range of ORP values.

In accordance with additional aspects of some embodiments, the method can include wirelessly receiving additional water quality data from a separate water quality monitor device configured to acquire the additional water quality data from the body of water, combining the water quality data with the additional water quality data, and transmitting the combined water quality data over the communication channel to the server.

In accordance with other aspects of some embodiments, the method can include providing at least two of the water quality monitoring devices including a first water quality monitoring device and a second water quality monitoring device, the first water quality monitoring device acquiring first water quality data from a first location in the body of water and transmitting the first water quality data over the communication channel to the server, the second water quality monitoring device acquiring second water quality data from a second location in the body of water, and transmitting the second water quality data over the communication channel to the server.

In accordance with further aspects of some embodiments, establishing the communication channel between the transceiver and the server can include the server hosting a publicly accessible website that displays the temperature data, the pH data, and the ORP data in real time.

In accordance with additional aspects of some embodiments, the method can include calibrating the temperature sensor based on a regression analysis, a 1-point calibration method, or a 2-point calibration method, calibrating the pH sensor based on a regression analysis, a 1-point calibration method, or a 2-point calibration method, and/or calibrating the ORP sensor based on a regression analysis, a 1-point calibration method, or a 2-point calibration method.

In accordance with other aspects of some embodiments, the water quality monitoring device can be a first water quality monitoring device, and the method can include providing a second water quality monitoring device including a second plurality of sensors.

In accordance with further aspects of some embodiments, the second plurality of sensors can include a second temperature sensor, a second a potential of hydrogen (pH) sensor, and a second oxidation-reduction potential (ORP) sensor, and the method further includes acquiring, by the second temperature sensor, second temperature data from the body of water; acquiring, by the second pH sensor, second pH data from the body of water; and acquiring, by the second ORP sensor, second ORP data from the body of water.

In accordance with additional aspects of some embodiments, the method can include associating the temperature data, the pH data, the ORP data, the second temperature data, the second pH data, and the second ORP data with a group identifier.

In accordance with other aspects of some embodiments, transmitting the water quality data to the server can include the first water quality monitoring device transmitting the temperature data, the pH data, and the ORP data to the server through the communication channel, and the second water quality monitoring device transmitting the second temperature data, the second pH data, and the second ORP data to the server through the communication channel, and the associating includes the server associating the temperature data, the pH data, the ORP data, the second temperature data, the second pH data, and the second ORP data with the group identifier.

In accordance with further aspects of some embodiments, transmitting the water quality data to the server can include the second water quality monitoring device transmitting the second temperature data, the second pH data, and the second ORP data to the first water quality monitoring device using the wireless protocol, where the water quality data includes the second temperature data, the second pH data, and the second ORP data, and where the associating includes the first water quality monitoring device associating the temperature data, the pH data, the ORP data, the second temperature data, the second pH data, and the second ORP data with the group identifier.

In accordance with additional aspects of some embodiments, the method can include calculating an average temperature based on the temperature data and the second temperature data, calculating an average pH based on the pH data and the second pH data, and/or calculating an average ORP based on the ORP data and the second ORP data.

In accordance with other aspects of some embodiments, the method can include calculating an average temperature based on the temperature data, calculating an average pH based on the pH data, and/or calculating an average ORP based on the ORP data.

In some embodiments, the techniques can be realized as a method of generating water quality data for a body of water, where the method can include providing a water quality monitoring device including a memory storing program instructions, one or more processors, a plurality of sensors including a temperature sensor, a potential of hydrogen (pH) sensor, and an oxidation-reduction potential (ORP) sensor, a transceiver, and a power source. The method includes calibrating at least one of the temperature sensor, the pH sensor, and the ORP sensor, configuring the transceiver to wirelessly communicate with an external device using a wireless protocol, submerging the temperature sensor, the pH sensor, and the ORP sensor into the body of water, acquiring, by the temperature sensor, temperature data from the body of water, acquiring, by the pH sensor, pH data from the body of water, acquiring, by the ORP sensor, ORP data from the body of water, generating the water quality data including the temperature data, the pH data, and the ORP data, and transmitting the water quality data to the external device.

In accordance with other aspects of some embodiments, providing the water quality monitoring device can include providing the plurality of sensors consisting of the temperature sensor, the pH sensor, and the ORP sensor.

In accordance with further aspects of some embodiments, the method can include coupling a renewable power generator to the water quality monitoring device, the renewable power generator including one or more photovoltaic panels, one or more wind turbines, and/or one or more hydroelectric generators.

In accordance with additional aspects of some embodiments, the temperature data, the pH data, and the ORP data can be acquired simultaneously from the body of water.

In accordance with other aspects of some embodiments, calibrating the temperature sensor can be based on a regression analysis, a 1-point calibration method, or a 2-point calibration method, calibrating the pH sensor is based on a regression analysis, a 1-point calibration method, or a 2-point calibration method, and calibrating the ORP sensor is based on a regression analysis, a 1-point calibration method, or a 2-point calibration method.

In accordance with further aspects of some embodiments, the method can include determining whether the temperature data includes a temperature value that exceeds a predetermined range of temperature values, determining whether the pH data includes a pH value that exceeds a predetermined range of pH values, determining whether the ORP data includes an ORP value that exceeds a predetermined range of ORP values, and generating an alert responsive to determining the temperature value exceeds the predetermined range of temperature values, determining the pH value exceeds the predetermined range of pH values, and/or determining the ORP value exceeds the predetermined ORP range of values.

In accordance with additional aspects of some embodiments, configuring the transceiver to wirelessly communicate with the external device using a wireless protocol can include operating the transceiver to wirelessly transmit the water quality data according to a timing schedule.

In accordance with other aspects of some embodiments, the water quality monitoring device can be a first water quality monitoring device, and the method can include providing a second water quality monitoring device including a second plurality of sensors.

In accordance with further aspects of some embodiments, the second plurality of sensors can include a second temperature sensor, a second a potential of hydrogen (pH) sensor, and a second oxidation-reduction potential (ORP) sensor, and the method further includes acquiring, by the second temperature sensor, second temperature data from the body of water, acquiring, by the second pH sensor, second pH data from the body of water, and acquiring, by the second ORP sensor, second ORP data from the body of water.

In accordance with additional aspects of some embodiments, the method can include associating the temperature data, the pH data, the ORP data, the second temperature data, the second pH data, and the second ORP data with a group identifier.

In accordance with other aspects of some embodiments, the method can include transmitting the water quality data to a server, which includes the first water quality monitoring device transmitting the temperature data, the pH data, and the ORP data to the server through a communication channel, and the second water quality monitoring device transmitting the second temperature data, the second pH data, and the second ORP data to the server through the communication channel, and the associating includes the server associating the temperature data, the pH data, the ORP data, the second temperature data, the second pH data, and the second ORP data with the group identifier.

In accordance with further aspects of some embodiments, transmitting the water quality data to the server can include the second water quality monitoring device transmitting the second temperature data, the second pH data, and the second ORP data to the first water quality monitoring device using the wireless protocol, the water quality data includes the second temperature data, the second pH data, and the second ORP data, and the associating includes the first water quality monitoring device associating the temperature data, the pH data, the ORP data, the second temperature data, the second pH data, and the second ORP data with the group identifier.

In accordance with additional aspects of some embodiments, the method can include calculating an average temperature based on the temperature data and the second temperature data, calculating an average pH based on the pH data and the second pH data, and/or calculating an average ORP based on the ORP data and the second ORP data.

In accordance with other aspects of some embodiments, the external device can be the second water quality monitoring device.

In accordance with further aspects of some embodiments, the external device can be a smartphone, a wireless router, or a cellular base station.

In accordance with additional aspects of some embodiments, the method can include calculating an average temperature based on the temperature data, calculating an average pH based on the pH data, and/or calculating an average ORP based on the ORP data.

In accordance with other aspects of some embodiments, the method can include establishing the communication channel between the external device and the server including the server hosting a publicly accessible website that displays the temperature data, the pH data, and the ORP data in real time.

In accordance with further aspects of some embodiments, the transceiver can be one of a Wi-Fi module and a cellular modem.

The present disclosure will now be described in more detail with reference to some embodiments thereof as shown in the accompanying drawings. While the present disclosure is described below with reference to some embodiments, it should be understood that the present disclosure is not limited thereto. Those of ordinary skill in the art having access to the teachings herein will recognize additional implementations, modifications, and embodiments, as well as other fields of use, which are within the scope of the present disclosure as described herein, and with respect to which the present disclosure may be of significant utility.

BRIEF DESCRIPTION OF THE DRAWINGS

To facilitate a fuller understanding of the present disclosure, reference is now made to the accompanying drawings, in which like elements are referenced with like numerals. These drawings should not be construed as limiting the present disclosure, but are intended to be illustrative only.

FIG. 7 shows a method of a water quality monitoring device acquiring and transmitting water quality data, in accordance with an embodiment of the present disclosure.

DETAILED DESCRIPTION OF EMBODIMENTS

Figure 1A:
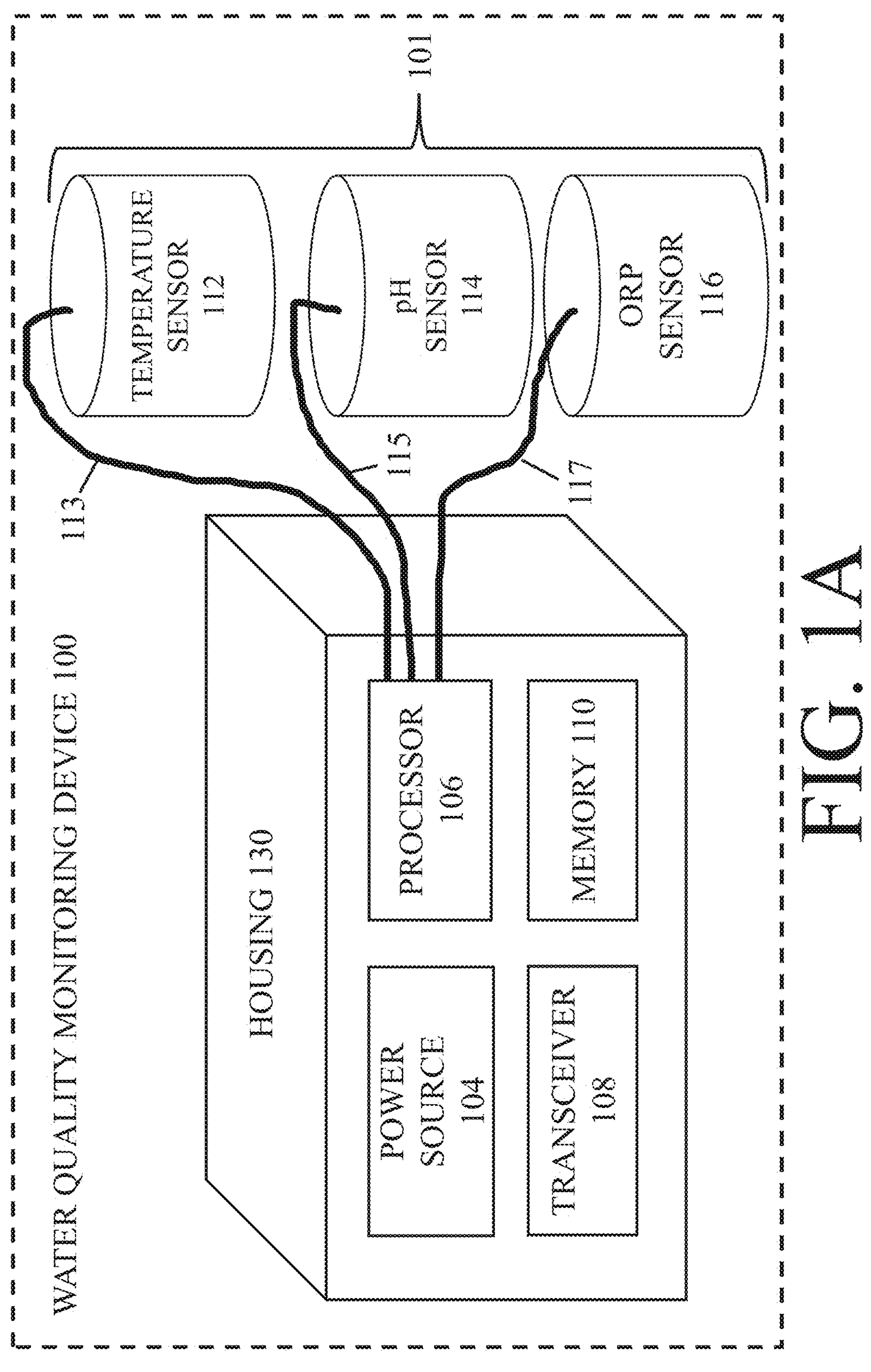
FIG. 1A shows a water quality monitoring device, in accordance with an embodiment of the present disclosure.

In the following detailed description, for purposes of explanation and not limitation, specific details are set forth in order to provide a better understanding of the present disclosure. It will be apparent to one skilled in the art that the present disclosure may be practiced in other embodiments that depart from these specific details.

The role of water quality in a healthy ecosystem cannot be understated. Clean, healthy water not only provides a safe drinking supply for communities but also supports biodiversity of microorganisms, plants and animals, including humans. Without a wide range of life in the Earth's many ecosystems, everything from the air humans breathe to the food humans eat may be negatively impacted, thereby impacting human health.

To respond to sudden ecological disasters like toxic industrial chemicals making their way into the nation's rivers, to have advanced knowledge that a local pond is unsafe to swim in for the day, or to study changes in aquatic ecosystems from migration and breeding patterns to harmful algal blooms, for example, one metric is of critical importance-water quality. However, there are numerous individual parameters that may fall under the umbrella of 'water quality.' For example, residual chlorine in drinking water is measured to determine if there is a sufficient amount of chlorine in the water to inactivate bacteria and certain viruses that can cause intestinal diseases in humans. Harmful pollutants, particularly metals and bacteria, may attach to particles suspended in water that humans may drink. To measure these pollutants, turbidity readings are acquired. Another parameter of water quality is electrical conductivity. Measuring the electrical conductivity of water cannot by itself identify a pollutant, but it can be used to help identify that there is a significant possibility of danger to invertebrates or fish. Of all the possible types of data to include in an assessment of water quality, selecting a subset of those data types that captures the most comprehensive and useful aspects of water quality, while at the same time making that acquired data available as soon as possible to as many people as possible at a cost most people could afford, is a significant challenge.

A comprehensive suite of sensors for acquiring a sufficient variety of water data ought to account for the most fundamental aspects of water itself. Thinking of water at the molecular or atomic level, there are three complimentary yet distinct perspectives. There is a physical perspective (e.g., moving atoms). There is a chemical perspective (e.g., chemical properties impacting electrical conductivity). There is also a biological perspective (e.g., cleanliness of water promotes biological life). To capture these three perspectives of water, embodiments herein utilize a suite of three specific sensors: a temperature sensor that is intrinsically linked to the physical perspective of water (e.g., temperature is a direct measure of the average kinetic energy of an atom), a potential of hydrogen (pH) sensor which utilizes electrical conductivity in water to directly measure chemical properties (e.g., acidity or alkalinity), and an oxidation-reduction potential (ORP) sensor that directly measures the ability of a body of water to sustain biological life (e.g., a high ORP value indicates excessive oxygen due to accumulation of waste products). Having determined the most comprehensive and efficient suite of sensors to deploy, a device employing such sensors, to be useful, ought to be portable and able to transmit its data as soon as it is acquired.

There are technical problems in the prior art of water quality monitoring devices as well that require technical solutions to achieve extensive and updated information on the health of natural water resources. The acquisition of water quality data from remote and difficult-to-reach locations or from many different locations simultaneously to track patterns and trends in water quality, for example, is limited by the ability to transmit that data to a location where it can be widely and quickly disseminated. Many lab-grade sensors that are used to measure ORP do not have any networking capabilities at all or are entirely dependent on a human operator being present to record the data as it is acquired. Requiring a person to be present drastically hampers portability. Some sensors are so cumbersome that they cannot be easily transported or left in the field because it would be too arduous to carry them to remote locations or retrieve them to recover their data. Embodiments described herein facilitate water quality monitoring devices that are small enough to be easily moved from one location to the next while still retaining the ability to acquire multiple parameters of water quality data at comparable levels to bulkier and costlier devices that measure a single parameter of water quality data.

Frequent transmission of water quality data is a persistent problem without any existing solution. Some sensors include local storage (e.g., using an SD card) because they are, by design, intended to be left to record data for a set period of time before the data is later retrieved and analyzed at a still later period of time. This approach clearly does not lend itself to fast, real time transmission of water quality data. By the time anyone can look at the data after retrieving the local storage and downloading the data, the data significantly loses its value of informing the public on the current status of their waterways. For example, with a device the uses local storage to retain water quality data, the stale data prohibits a prompt warning of urgent ecological problems like a chemical spill that began shortly after the device was deployed in the field but only discovered days, weeks, or months later when the data is finally analyzed, costing valuable time in preventing further damage to the environment. Embodiments described herein, solve this technological problem by employing a technical solution with an efficient and streamlined design.

With the proliferation of low power and inexpensive wireless chips, such as Wi-Fi modules (e.g., a standalone circuit that transmits and receives data per a Wi-Fi standard), a water quality monitoring device can communicate with a network via a Wi-Fi communication channel to transmit its data instantly or in real time. Embodiments are not limited to Wi-Fi as a wireless means of communication and include embodiments using cellular (e.g., LTE, 5G) transceivers as well. One benefit of Wi-Fi over cellular is that using Wi-Fi does not require a fee to access the Internet. Water quality monitoring devices that employ wireless transmission technologies having longer range compared to Wi-Fi (e.g., LTE) have the benefit of being deployable in more remote areas that do not have at least one device connected to a Wi-Fi network, with the drawback of having an additional barrier to entry (e.g., cellular subscription service). Wi-Fi as well as cellular embodiments are capable of real time transmission of water quality data once a communication channel to the Internet is established.

As used herein, the terms "real time," "instantly," "simultaneously" or the like in the context of transmitting water quality data are intended to describe electronic components that are carrying out their respective processes and operations as fast as they can only being limited by physical restraints in the real world. For example, a water quality monitoring device that transmits its sensor data in "real time" means that the device is programmed to transmit its sensor data as soon as the data is acquired pending differences in processor clock speeds, electrical resistance of wires carrying analog voltage signals from sensors, atmospheric anomalies between transmitter and receiver, and so forth.

Despite the trend of electronic devices becoming 'smarter' as new versions of electronic devices iterate through the years (e.g., the newest version has more processing power, more resolution, more storage capacity), storing the acquired water quality data is detrimental for a variety of reasons. First, all computer hardware has a cost and memory modules are no exception. Even though local storage options like SD cards have become more affordable, constructing circuit boards at scale to incorporate the ability to receive an SD card could make the entire production unfeasible and add to growing costs that may become so high that the average person could not afford the end device in the first place. So, an important and unintuitive insight into the development of the water quality monitoring devices described herein is that not including long-term or non-volatile storage, like an SD card, reduces manufacturing cost and also creates massive benefits. Without storing the data, and instead immediately transmitting it, sensor data is guaranteed to be as up-to-the minute as possible and not be stale or out of date. Furthermore, without requiring local storage for subsequent data retrieval, like an SD card, water quality monitoring devices are cheaper to manufacture and therefore are more economically attainable for more people.

A water quality monitoring device 100 is shown in FIG. 1A as including a housing 130 encasing a power source 104, a processor 106, a transceiver 108, and a memory 110. In certain embodiments, the housing 130 forms a waterproof enclosure that protects the encased components from being damaged by water or other natural elements in outdoor areas or aquatic environments. The material of the housing 130 is, in at least one example, plastic, which favorably balances cost with resilience to the elements. The water quality monitoring device 100 includes three sensors: a temperature sensor 112, a pH sensor 114, and an ORP sensor 116. These three sensors are a plurality of sensors 101 that form a comprehensive suite of sensors for acquiring the most useful water quality data as described above. The plurality of sensors 101 is coupled to a processor 106 within the water quality monitoring device 100.

The power source 104 is configured to provide electrical power to the processor 106, the transceiver 108, the memory 110, and the plurality of sensors 101. When the plurality of sensors 101 is connected to the processor 106 and the processor 106 is powered by the power source 104, the processor 106 is able to receive live water quality sensor data from the plurality of sensors 101 and perform various operations on the received water quality data (e.g., controlling the transceiver 108 to wirelessly transmit the water quality data).

The temperature sensor 112 is coupled to processor 106 via a wired connection 113 (e.g., one or more conductive wires). The pH sensor 114 is coupled to processor 106 via a wired connection 115 (e.g., one or more conductive wires). The ORP sensor 116 is coupled to processor 106 via a wired connection 117 (e.g., one or more conductive wires). Each of the wired connections 113, 115, 117 includes, in at least one embodiment, three distinct wired connections, one of the three wired connections connected to an input voltage terminal of the processor 106 (e.g., VCC), another of the three wired connections connected to a ground terminal of the processor 106 (e.g., GND), and the third wired connection connected to an analog input of the processor 106. The analog input carries an analog voltage signal corresponding to water quality data of the respective sensor. For example, the analog input of the processor 106 coupled to the ORP sensor 116 receives ORP data as part of the water quality data produced by the plurality of sensors 101.

The power source 104 is, in certain embodiments, one or more batteries connected in parallel or in series to achieve a total level of power at least as great as a minimum amount of power required by the processor 106 to operate nominally. The one or more batteries may be non-rechargeable (e.g., alkaline) or rechargeable (e.g., lithium-ion).

To reduce manufacturing cost (and thereby the ultimate purchase price for a buyer) and minimize the complexity of the water quality monitoring device 100 (e.g., one less component that could fail), in at least some examples, the memory 110 is configured to only store program instructions for the processor 106 to execute to acquire and transmit water quality data from the plurality of sensors 101. In this manner, the processor 106 at most buffers the water quality data until the transceiver 108 is finished transmitting the previous acquisition of water quality data without storing any water quality data for a long term (e.g., not stored in non-volatile memory or a local storage device such as an SD card).

While the processor 106 and the memory 110 are shown in FIG. 1A as being separate functional blocks, it is understood that embodiments include one or more of the processor 106, the memory 110, and the transceiver 108 being implemented on a single chip, board, or module. In an example, the processor 106 and the memory 110 are included in a single microcontroller. To program the processor 106, any suitable programming language may be used. In at least one example, the programming language is one of C++, C, Java, and Python.

Figure 1B:
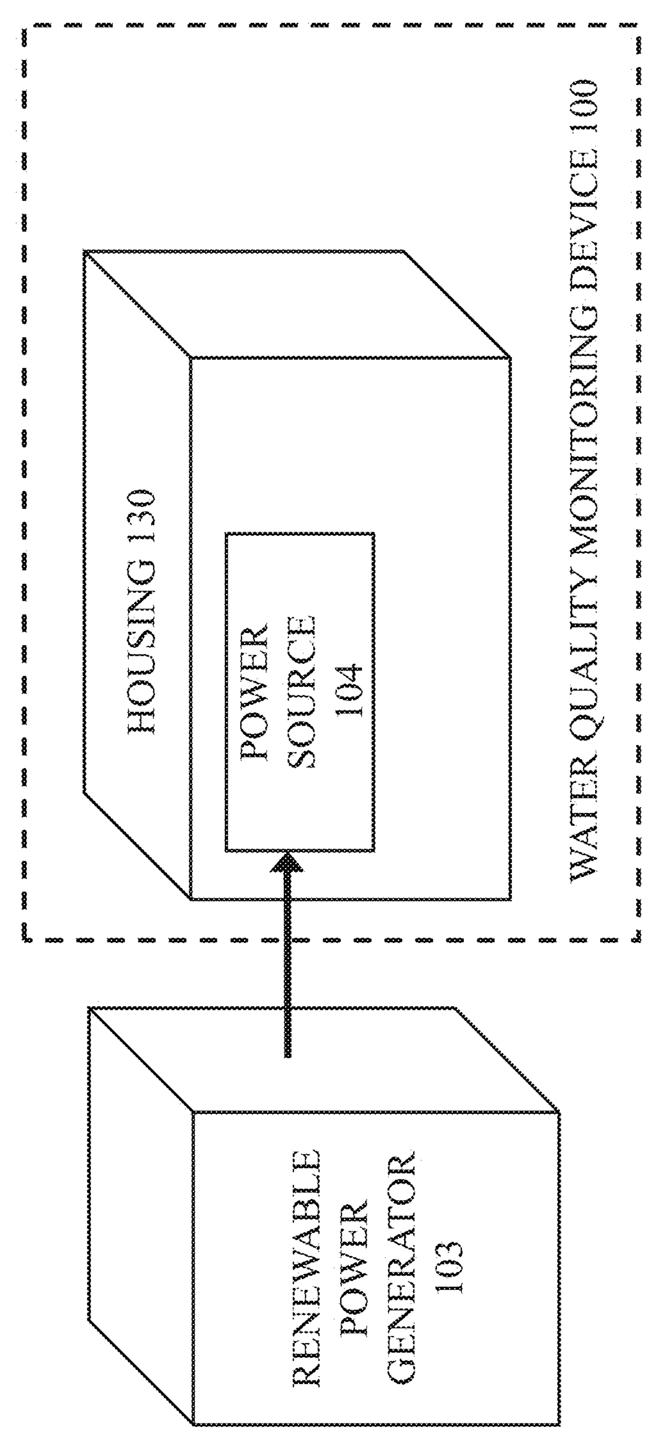
FIG. 1B shows a renewable power generator coupled to the water quality monitoring device in FIG. 1A, in accordance with an embodiment of the present disclosure.

To extend the operational lifespan of the water quality monitoring device 100, a renewable power generator 103 is coupled to the power source 104 to recharge any rechargeable batteries of the power source 104 as shown in FIG. 1B. To attach the renewable power generator 103 to the water quality monitoring device 100, some embodiments of the housing 130 include a plug or waterproof port that is opened by a user to reveal a conductive element that conducts power from the renewable power generator 103 to the power source 104, via, for example, a direct connection between power generator 103 and power source 104 or a length of cable attached between power generator 103 and power source 104. Providing a renewable source of power extends the amount of time the water quality monitoring device 100 can operate without replenishment of the power source 104, thereby increasing its portability because people are more inclined to place the device in a location that is physically challenging to reach that they do not have to return to as often to service (e.g., replace or recharge batteries).

Depending on the environment where the water quality monitoring device 100 is deployed, the choice of one type of renewable power generator 103 over another may be more optimal. In one example, the renewable power generator 104 can be one or more solar panels where the water quality monitoring device is deployed to monitor a river in a region that receives a significant amount of sunlight (e.g., the Colorado river flowing between Nevada and Arizona).

In environments that lack sufficient sunlight for solar panels to be beneficial, the renewable power generator 103 can utilize energy contained within the body of water being monitored. For example, a hydroelectric generator in the power generator 103 may incorporate a turbine which rotates due to water flowing across it, which in turn spins a generator that ultimately produces electricity, which is provided to the power source 104. In other examples, the environment may contain enough average windspeed for a wind turbine to be incorporated into the renewable power generator 103 to harness renewable energy from the wind in a matter analogous to how a hydroelectric generator harnesses renewable energy from flowing water. Embodiments described herein are not limited to only the aforementioned types of renewable power.

Figure 2:
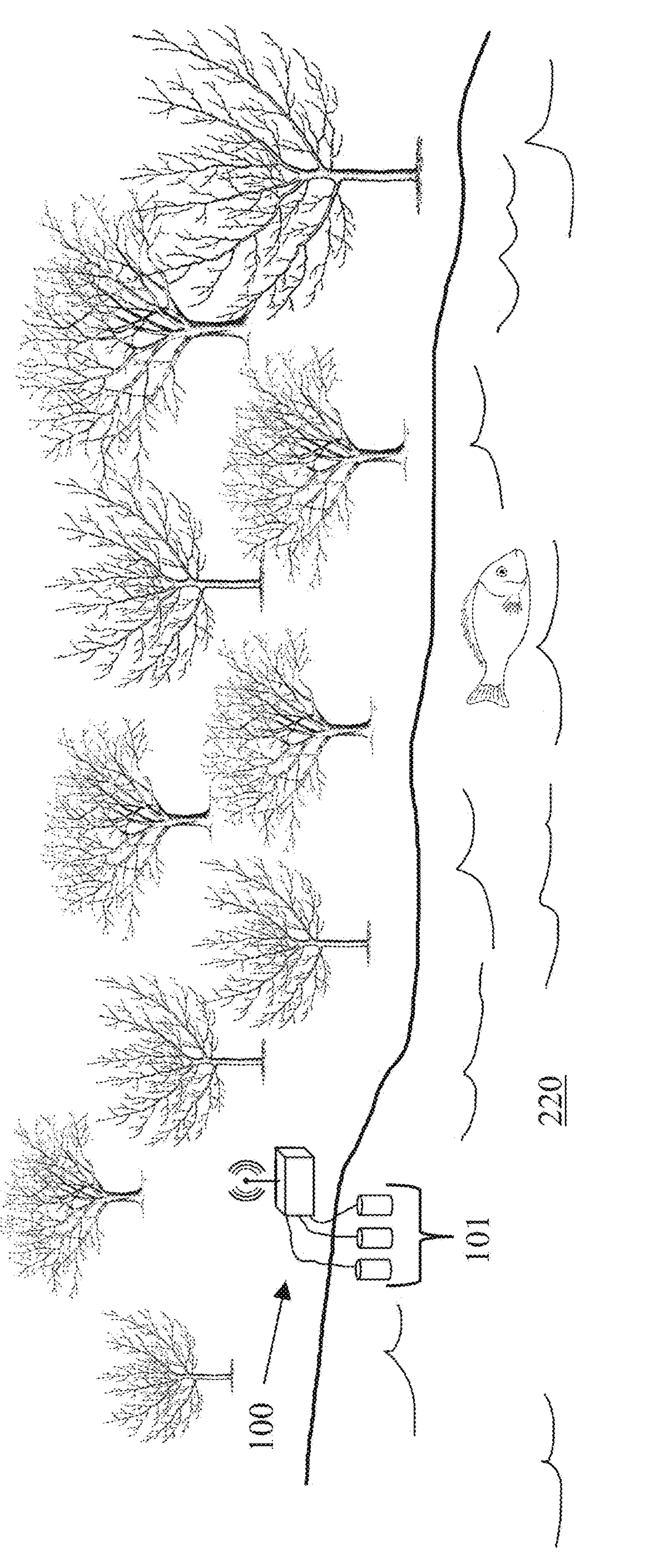
FIG. 2 shows a water quality monitoring device deployed in a body of water in an aquatic ecosystem, in accordance with an embodiment of the present disclosure.

One use case of the water quality monitoring device 100 is exemplified in FIG. 2. Once the water quality monitoring device 100 is calibrated (discussed in further detail below), the plurality of sensors 101 is submerged into a body of water 220 to obtain water quality data therefrom. To monitor multiple points of a body of water and/or to generate more detailed water quality data (e.g., an average, a trend in water quality from one region to another) another use case is exemplified in FIG. 3, where a plurality of water quality monitoring devices (e.g., one or more the water quality monitoring device 100) are deployed to acquire water quality data from a body of water 320. The plurality of water quality monitoring devices includes a first water quality monitoring device 301, a second water quality monitoring device 302, a third water quality monitoring device 303, and a fourth water quality monitoring device 304. It is understood that providing four water quality monitoring devices is one example and other amounts of water quality monitoring devices may be employed in a similar manner (e.g., 2, 3 or 5+ devices). Furthermore, while each the water quality monitoring devices 301, 302, 303, 304 shown in FIG. 3 is identical in structure to the water quality monitoring device 100, it is understood that other embodiments can include water quality monitoring devices with different structures (e.g., one device includes a rechargeable battery as its power source while another includes a non-rechargeable battery as its power source).

To acquire water quality data from two locations of the body of water 320, as an example, the plurality of sensors of the first water quality monitoring device 301 is submerged in the body of water 320 at a first location and the plurality of sensors of the second water quality monitoring device 302 is submerged in the body of water 320 at a second location. To facilitate the real time acquisition and dissemination of water quality data, each of the plurality of water quality monitoring devices is configurable to communicate with a wireless device 306. The wireless device 306 is configured to establish a communication channel 309 between any number of the plurality of water quality monitoring devices, a sever 310, and a user device 312.

Figure 3:
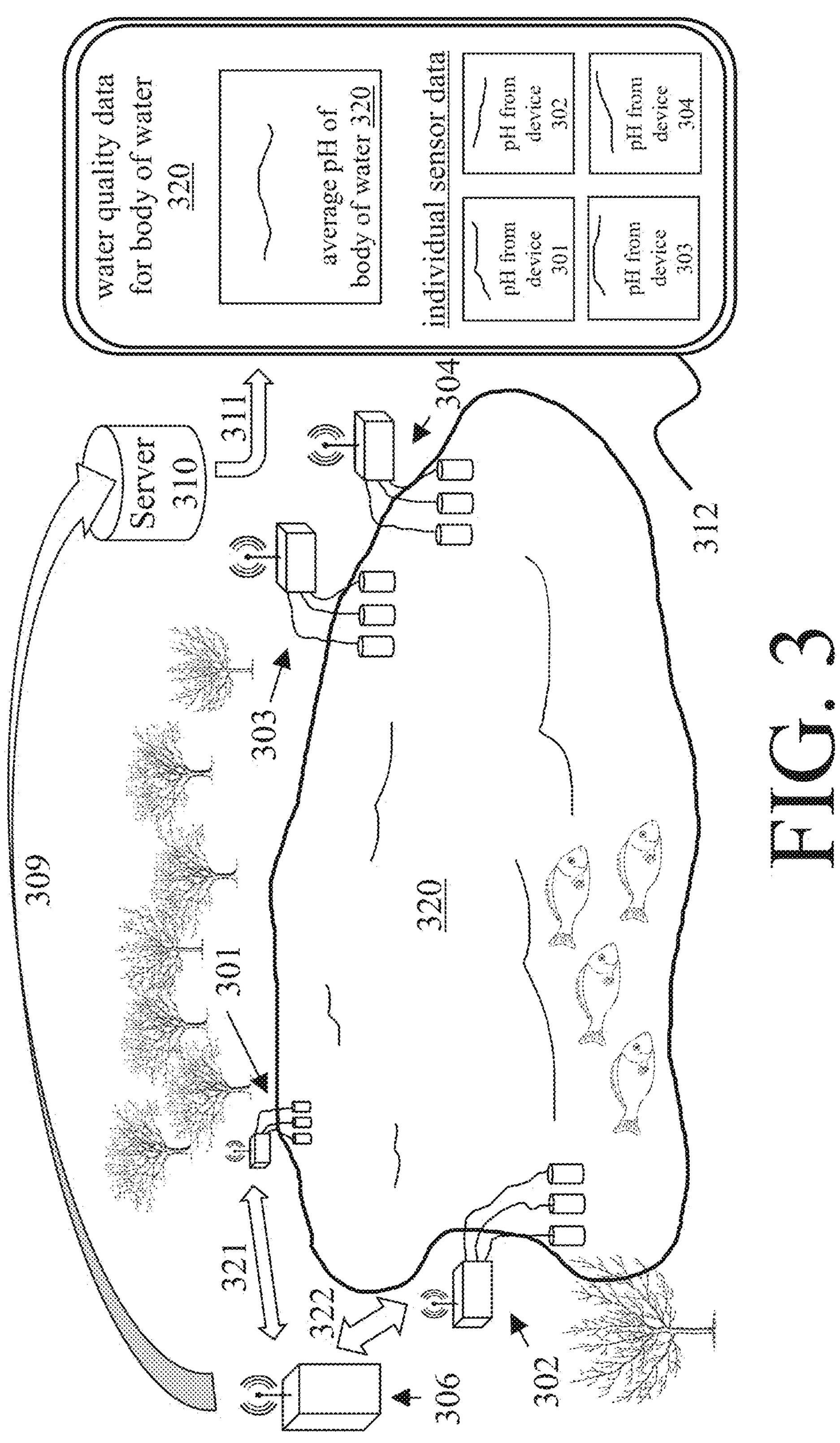
FIG. 3 shows a group of water quality monitoring devices deployed in a body of water in an aquatic ecosystem, in accordance with an embodiment of the present disclosure.

FIG. 3 depicts a plurality of communication channels including one or more wired connections and/or one or more wireless connections. A first communication channel 309 communicatively connects the wireless device 306 and the server 310. A second communication channel 311 communicatively connects the server 310 with the user device 312. Multiple communications channels, such as the first communication channel and the second communication channel, may transfer the same data from a source device to a destination device (e.g., from the first water quality monitoring device 301 to the user device 312). A series of communication channels may be referred to as a single 'communication channel.' Each communication channel in a series of communication channels may use the same or difference communication protocol. In an example, water quality monitoring devices may use a Wi-Fi protocol to wirelessly transmit water quality data to one or more wireless devices (e.g., the wireless device 306), which in turn uses the same or different Wi-Fi protocol to transfer the water quality data to the server 310, which in turn transmits the water quality data using an https connection. Furthermore, it is understood that FIG. 3 illustrates paths of data communication that are simplified for better understanding, and that embodiments include additional devices included in the paths of communication. For example, the wireless device 306 may wirelessly connect to a municipal Wi-Fi network, which in turn transmits the data along wired connections to a node provided by an internet service provider (ISP), which in turn transmits the data to the server.

As first water quality data is acquired from a sample of a first location in the body of water 320 by the plurality of sensors of first water quality monitoring device 301, the processor therein operates the transceiver therein to wirelessly transmit the first water quality data to the server 310 via a direct wireless connection 321 to the wireless device 306. Similarly, second water quality data from a sample of a second location is acquired by the plurality of sensors of the second water quality monitoring device 302 and wirelessly transmitted to the server 310 via a direct wireless connection 322 to the wireless device 306. In one example, the direct wireless connections 321, 322 with the wireless device 306 utilize a Wi-Fi protocol (e.g., operating at 2.4 GHz or 5 GHz implementing 802.11a, 802.11b, 802.11g, 802.11n, 802.11ac, or 802.11ax). In another example, a wireless device is a cellular tower or cellular base station configured to communicate via a cellular protocol (e.g., LTE) with corresponding cellular modems in connected water quality monitoring devices.

The server 310 can receive the first water quality data, the second water quality data, and other collected water quality data from wireless device 306 via the first communication channel 309. In at least one example, the direct wireless connections 321, 322, the first communication channel 309 and the second communication channel 311 utilize the wireless protocol of 802.11n.

The server 310 is accessible over the Internet, meaning once the water quality data has reached the server 310, it may be immediately disseminated to any device connected to the Internet and having access to the server 310. To promote the proliferation of extensive and updated water quality data, the server 310 is configured, in at least some examples, to host a publicly available website (i.e., not located behind a pay wall). By providing unrestricted access to a website that consolidates water quality data from any number of water quality monitoring devices, anyone can easily and quickly see real time data directly from the devices (e.g., in embedded graphs on the website). To make the water quality data as accessible as possible, the website includes, in certain examples, explanatory details on each water quality parameter to enhance the public knowledge about important aspects of bodies of water in their communities. In some examples, raw water quality data provided by the sensors to the website is made available to download for free in multiple different file formats.

In building a website as described above, a user may register a domain name for the website to be hosted by one provider and utilize one or more Internet of Things (IoT) based tools from a different provider to embed graphs, plots, or other graphics into the website to display water quality data in real time. The provider and the IoT based tool may be hosted on different servers or at different network locations. Accordingly, the server 310 is, in some embodiments, the server that hosts the website and a different server handles transferring live sensor data from water quality monitoring devices to the embedded features hosted by the server 310. In other embodiments, the server 310 handles both of these functions. The server 310 in other embodiments handles the IoT based tool while a different server hosts the website. Users, in certain examples, may utilize an open IoT platform (e.g., ThingSpeak) to establish a communication channel between any of the plurality of water quality monitoring devices and the server 310, which is accessible by any number of devices including the user device 312. For example, a user may configure the open IoT platform to obtain water quality data from specific water quality monitoring devices transmitted through a communication channel including the first communication channel 309, the server 310, and the second communication channel 311.

The user device 312 is shown in FIG. 3 as a smartphone including one or more processors, a memory storing instructions to be executed by the one or more processors, and a touch screen displaying water quality data. The touch screen may display content of a browser, an app, or any other program executable by the one or more processors. The displayed content, in at least some examples, includes a graphical user interface (GUI) including user-selectable elements to navigate and manipulate the displayed content (e.g., hyperlinks, images, menus, radio buttons, and the like). However, other embodiments include the user device 312 being a desktop computer, laptop, server, or any other device with the function of allowing a person to access content on the Internet.

Although not shown, it is understood that the third water quality monitoring device 303 and the fourth water quality monitoring device 304 may have direct wireless connections to the wireless device 306. In other examples, a water quality monitoring device communicates its acquired water quality data directly to a user device without transmitting the data through a server. Certain users may wish to gather water quality data for their own purposes without wanting to share the data with the public. For example, a user may simply wish to monitor the health of a private pond in their backward by using their smartphone to wirelessly connect to, a water quality monitoring device via a smartphone wireless protocol (e.g., Wi-Fi, Bluetooth).

FIG. 3 demonstrates how the more devices that are deployed, the more valuable the acquired water data becomes. For merely a single user, by deploying four water quality monitoring devices at the body of water 320, the user is able to gain insights that a single device could not achieve on its own. For example, the user is able to monitor how pH levels may be suitable for sustaining wildlife in one region of the body of water 320 but not in another due to contamination that is localized to a specific area of the body of water 320. The user can then pinpoint the source of the contamination and take appropriate steps to remediate it or bring it to the attention of authorities or the public. pH can be used to track ocean acidification, one of the largest indicators of climate change, being directly correlated to carbon dioxide emissions. pH also affects the development of marine organisms like crabs and coral, which are tied to massive seafood markets, thereby providing an economic incentive to prevent the marine animal populations from declining to dangerously low levels. PH levels are used as an example and it is understood that the water quality data for the body of water 320 may include temperature, pH, and ORP data displayed together in any number of ways by one of ordinary skill in the art. For example, a user may choose to display average temperature of the body of water 320 and device-specific levels of pH and ORP.

Figure 4:
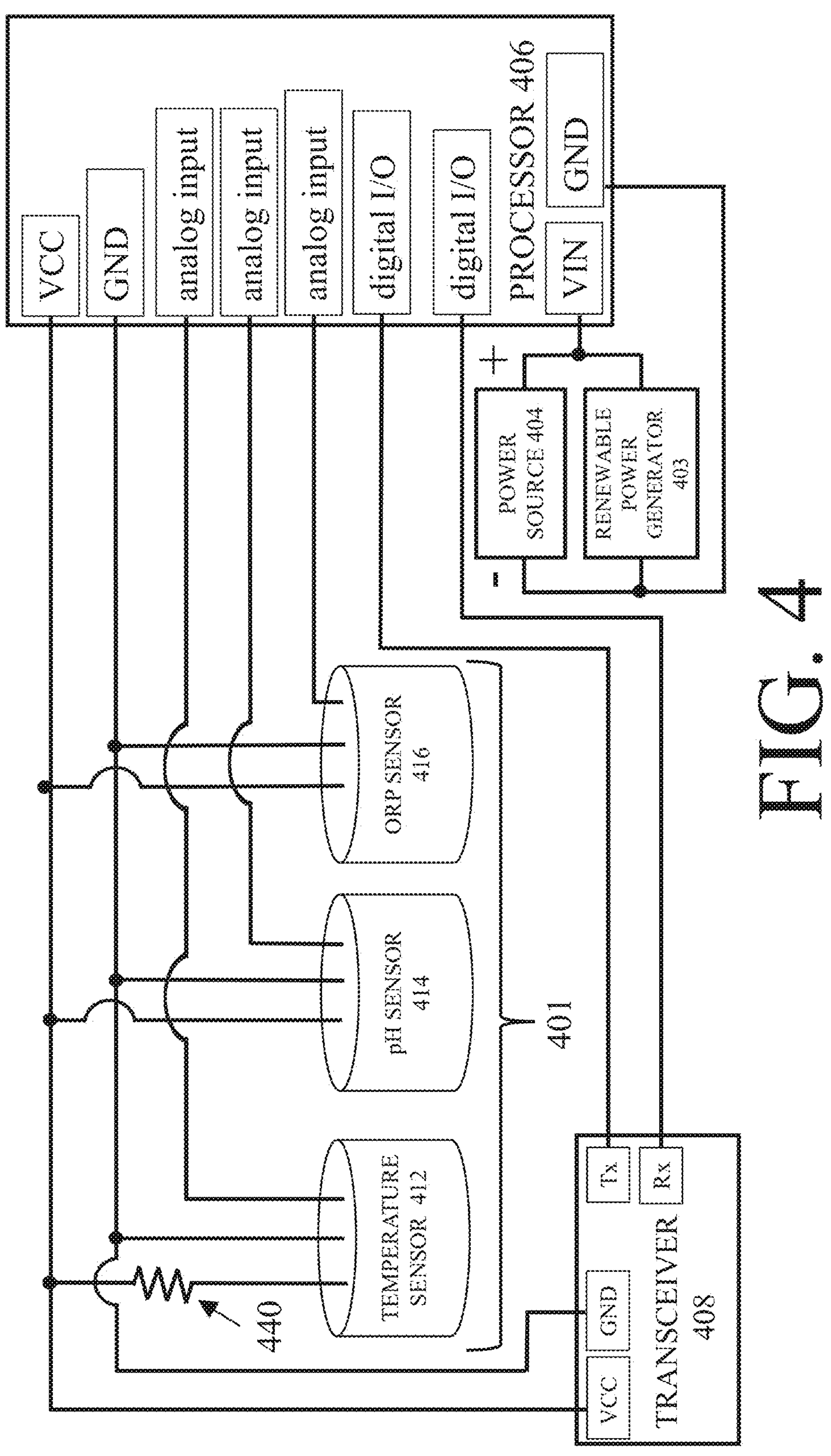
FIG. 4 shows a circuit diagram of a water quality monitoring device, in accordance with an embodiment of the present disclosure.

To create a water quality monitoring device as described above, one example of a circuit diagram of a water quality monitoring device is provided in FIG. 4. Embodiments include customized transceivers, sensor suites, power sources, renewable power generators, and/or processors that do not depart from the overall functionality described in reference to the circuit diagram of FIG. 4.

The circuit diagram in FIG. 4 includes a renewable power generator 403, a power source 404, processor 406, a transceiver 408, a resistive element 440, and a plurality of sensors 401 including a temperature sensor 412, a pH sensor 414, and an ORP sensor 416. In at least one example of the circuit diagram, the processor 406 is a programmable computer (e.g., Arduino Uno) that is programmed to not store any acquired water quality data. The transceiver 408, in this example is a Wi-Fi chip (e.g., an ESP8266-01S Wi-Fi chip). Keeping with this example, the power source 104 provides at least 5 volts of DC power to the processor 406 (e.g., a 4500 mAh 12V battery), the renewable power generator 403 is a solar panel (e.g., a 20 W solar panel), the resistive element 440 is a resistor (e.g., 4.7 k ohm), the temperature sensor 412 is a temperature sensor (e.g., DS18B20 waterproof temperature probe), the pH sensor 414 is a pH sensor (e.g., Gravity Analog pH Sensor and Circuit from Atlas Scientific, a 6565 ph/ORP sensor from YSI (Xylem)), and the ORP sensor is an ORP sensor (e.g., Gravity Analog ORP Sensor and Circuit from Atlas Scientific, a 6565 ph/ORP sensor from YSI (Xylem)).

Each sensor of the plurality of sensors 401 is individually connected to a respective analog input of the processor 406. The plurality of sensors 401 is connected to VCC and GND terminals of the processor 406, with the resistive element 440 coupled between the temperature sensor 412 and the VCC terminal of the processor 406. The transceiver 408 includes VCC and ground (GND) terminals coupled to corresponding VCC and GND terminals of the processor 406. The transceiver 408 also includes a transmission (Tx) terminal and a receiving (Rx) terminal that are each respectively connected to digital I/O ports of the processor 406. The power source 404 is connected in parallel with the renewable power generator 403 between an input voltage terminal and an additional GND terminal of the processor 406.

Having provided detailed information to inform one of ordinary skill in the art how to construct a water quality monitoring device, methods of monitoring a body of water using such devices will now be described with reference to FIGS. 5-7.

Figure 5:
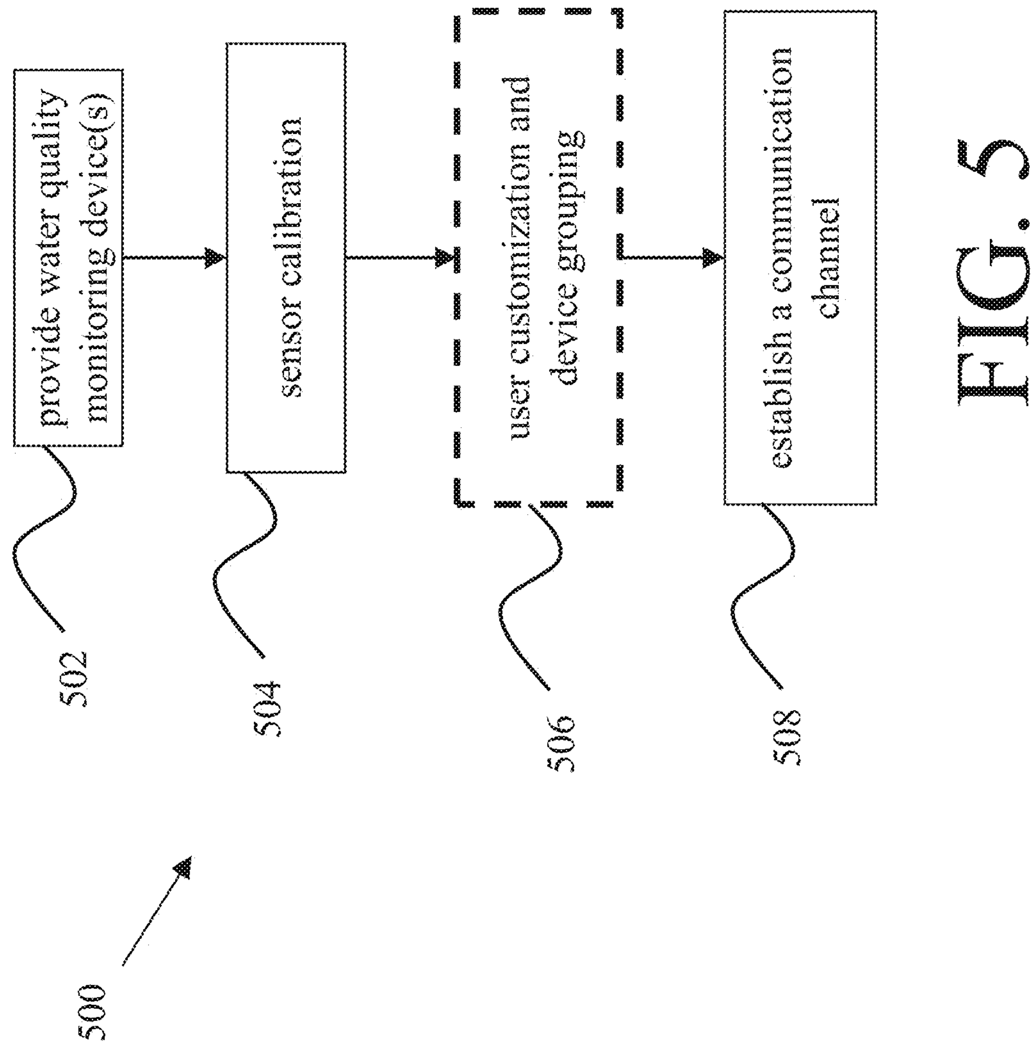
FIG. 5 shows a method of configuring a water quality monitoring device, in accordance with an embodiment of the present disclosure.

A method 500 is shown in FIG. 5 that includes steps for setting up and calibrating any of the water quality devices described above. The method 500 includes a step 502 to provide one or more water quality devices (depending on the particular user application), followed by a step 504 to calibrate the sensors, an optional step 506 to customize the presentation of the water quality data and/or how multiple devices may be grouped together for further processing, and a step 508 to establish a communication channel with a server (e.g., the server 310).

In the step 502, the hardware of a water quality monitoring device (e.g., the water quality monitoring device 100) is assembled (e.g., using the circuit diagram in FIG. 4). Once the hardware is assembled including the plurality of sensors (e.g., the plurality of sensors 401), all of the hardware excluding any renewable power generator or sensors are encapsulated in a housing (e.g., the housing 130). If the environment where the water quality monitoring device(s) is expected to be deployed may subject the housing to water (e.g., a rainy region, the housing being shaped into a buoy that floats on a body of water), then the housing is waterproofed (e.g., using a sealant, gasket, or similar material) or at least made water resistant. Before submerging the plurality of sensors in a body of water, the processor of each water quality monitoring device is programmed so that the plurality of sensors can be calibrated where needed.

In the step 504, the plurality of sensors is calibrated where needed. Certain sensors, particularly temperature sensors, do not require calibration before obtaining accurate temperature data. As such, in at least one example of step 504, calibration of the temperature sensor is omitted while the remainder of the plurality of sensors (e.g., the pH sensor 114 and the ORP sensor 116) are calibrated. Calibration may be performed in a convenient location before any device is deployed in the field. To calibrate any of the plurality of sensors, a 1-point calibration method, a 2-point calibration method, or a regression analysis may be used, though embodiments are not limited to such calibration methods. Additionally, each of the plurality of sensors may be calibrated in any order. FIG. 6 shows one example of an order of calibrating the plurality of sensors.

Figure 6:
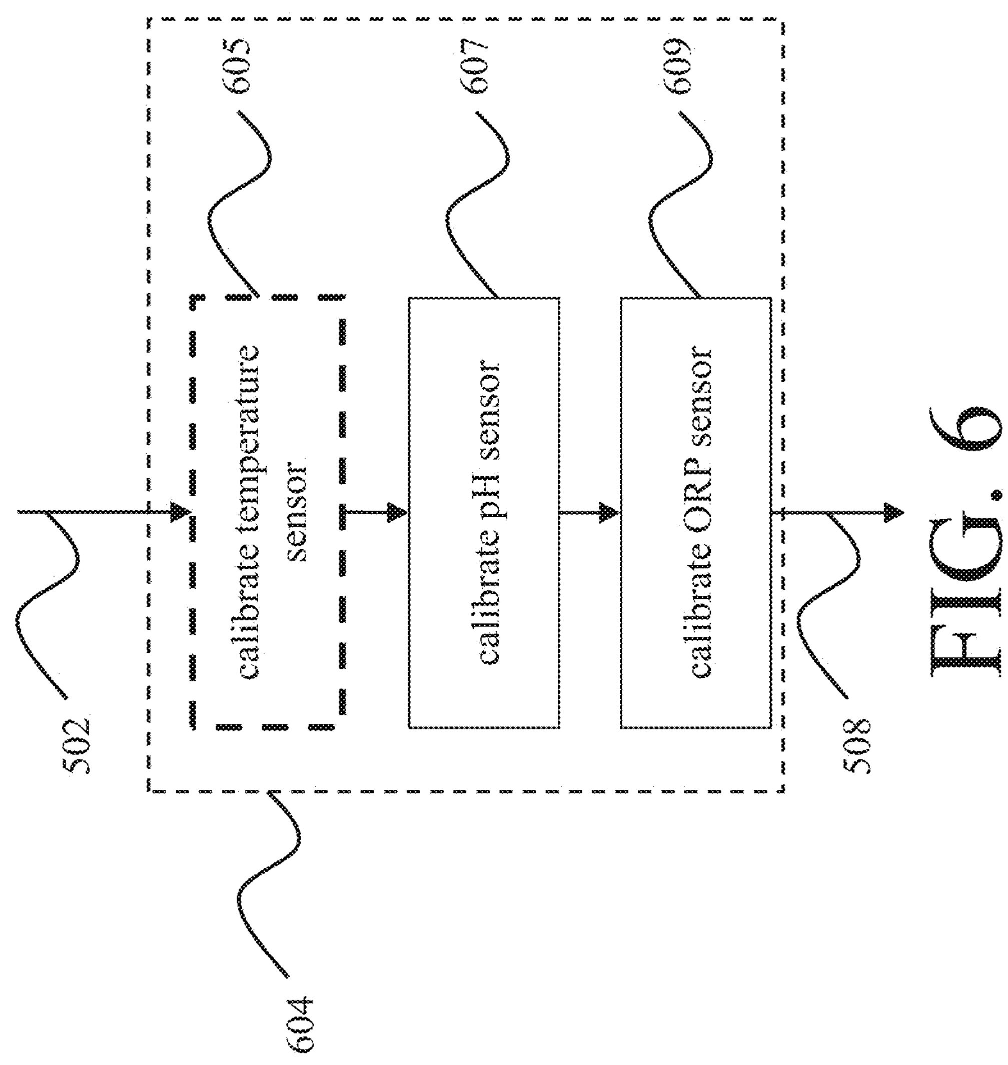
FIG. 6 shows a method of calibrating sensors of a water quality monitoring device, in accordance with an embodiment of the present disclosure.

A calibration method 604 is shown in FIG. 6, where the calibration method 604 is performed after the step 502 and before the step 508. The calibration method 604 includes a step 605, followed by a step 607, which is followed by a step 609. The calibration method 604 first optionally calibrates the temperature sensor in the step 605. This may be necessary if, for example, when the temperature sensor is precise but not accurate, which is remedied by accounting for an offset error in the programming of the processor. After the temperature sensor is optionally calibrated in the step 605, the pH sensor is calibrated in the step 607 and the ORP sensor is calibrated in the step 609.

The processor is programmed in the step 504 or the step 604 to account for the sensor calibration parameters. For example, to calibrate the pH sensor in the step 607, the pH sensor is submerged in a buffer solution of known pH value (e.g., a pH of 7) to obtain a voltage reading for a first calibration point. Then the pH sensor is washed and inserted into a buffer solution of a different known pH value (e.g., a pH of 4). Another voltage reading is obtained when the sensor values are stable. Using the two calibration points, two-point calibration is performed in the step 607 to generate a function that relates voltages produced by the pH sensor and read by the processor to their proper pH values.

Because a pH sensor produces an electrical signal proportional to physical or chemical properties (e.g., acidity) of the liquid it is immersed in, two-point calibration is suitable for pH sensor calibration. ORP sensor calibration, on the other hand, does not have the same one-to-one correspondence with properties of the liquid the ORP sensor is immersed in. As such, in the step 609, a one-point calibration method for the ORP sensors is used because the acquired ORP values are based on an electrical potential, specifically the voltage difference of the ORP electrode and a reference electrode. Because this difference typically follows a known standard (e.g., 200 mV at room temperature), it is more efficient to use 1-point calibration over 2-point calibration for calibrating the ORP sensor because 2-point calibration likely will not increase the sensor's accuracy to an appreciable degree. As with the pH sensor calibration, the processor is programmed in the step 604 to incorporate a function derived from the calibration method that relates voltages interpreted by the processor to specific ORP values.

If the wireless device (e.g., the wireless device 306) that will be the communication intermediary between the plurality of sensors and the server (e.g., the server 310) is available (or the registration procedure is known a priori) before deploying the sensors in the field, then the processor may further be programmed in the step 504 to have the necessary credentials to establish a wireless link between the server, the wireless device, and any of the water quality monitoring devices to be deployed. In other embodiments, the processor is programmed with credentials, network address, or other identifying information to eventually publish the water quality data to a network location accessible on the Internet (e.g., the server 310) in the step 502, the step 506, or the step 508.

Embodiments include water quality monitoring devices that transmit or relay water quality data between each other before the water quality data is transferred to a server or other network location. For example, in the step 502 or the step 504, the processor of a first water quality monitoring device may be programmed to establish communication with and send its water quality data to a second water quality monitoring device in the event the first device loses communication with the server for a threshold amount of time (e.g., no connection for 5 minutes). Otherwise, the user programs each processor to report its respective water quality data at predetermined time intervals. Ideally, the predetermined intervals would be as small as possible. However, the smaller the interval, the faster the device will consume available power and the sooner the device may not be capable of reporting water quality data at all. A predetermined interval of acquiring new or additional water quality data every 10 seconds is one example of a suitable tradeoff between getting the most current data and conserving available power to maximize the operational life span (i.e., how long the device can operate nominally before not having enough power to transmit any water quality data). In the case of a water quality monitoring device being programmed to report water quality data every 10 seconds, the processing that includes the data acquisition and reporting/transmission of the data occurs in real time (i.e., as soon as the processor is instructed to acquire a new sample of water quality data, its next operation is to transmit that data, and then wait 10 seconds before repeating the acquisition and transmission of the next sample). It is understood that optimal periods for delaying the acquisition of new water quality data may depend on a number of factories including total capacity of the available power source, a particular trend being studied, and so forth. As such, delays of 5 seconds, 20 seconds, and so forth are contemplated herein.

The optional step 506 may be performed before or after the step 504. In the step 506, the user programs the open IoT platform, website, or other Internet-based tool to present the water quality data in a way that suits their particular needs and use case. For example, the user may desire to create a public website that shows average ORP values along a particular stretch of a river. To do so, the user may place a first group of water quality monitoring devices upstream, a second group downstream, and a third group in between, and then calculate and average ORP value for each of the three groups. Then, the user may embed a chart on a website to provide a simple and effective visual representation of the health of the river along the particular section. In some examples a group of water quality monitoring devices is electronically grouped together using a group identifier (e.g., a piece of data that associates multiple devices together with a single identity or label).

After calibration is complete, the method 500 proceeds to the step 508. In the step 508, the plurality of sensors of each water quality monitoring device is submerged into the body of water at a location specified by the user. To ensure the sensors remain submerged, in some embodiments, weights may be added to keep the buoyant force acting on each sensor less than the weight of each sensor. The water quality monitoring devices are connected to any available renewable power generator (e.g., the renewable power generator 103) and powered on. The user may then confirm the device is operating nominally almost immediately by accessing the server (e.g., through a public website) to see the water quality data being published in real time.

The website may also be configured generate an alert based on the water quality data containing temperature, pH, and/or ORP values that deviate significantly enough from nominal or expected values to justify generating the alert to call attention to an issue deemed important by a user. For example a user may want to set an alert for when temperature values of a river supplying a hydroelectric dam are nearing freezing temperatures. Accordingly, responsive to determining the water quality data indicates a temperature value that exceeds a predetermined range of temperature values (e.g., below 33 degrees Fahrenheit), an alert is generated. Similarly, if a pH value exceeds a predetermined range of pH values (e.g., 8 or higher), then an alert may be generated to inform the public that the body of water is unsafe to swim in. If an ORP value exceeds a predetermined range of ORP values (e.g., outside the range of 300 to 500 millivolts), then an alert may be generated that aquatic wildlife in the body of water being tested may be in danger of adverse health effects.

Once a water quality monitoring device is calibrated and ready to wirelessly transmit its data (e.g., by completing the method 500), the device performs an operational method to acquire and transmit water quality data in real time. FIG. 7 show an operational method 700 which includes a step 702, a step 704, an optional condition 705. In the step 702, the water quality monitoring device acquires a sample of water quality data. In an example, a processor of the water quality monitoring device obtains temperature data, pH data, and ORP data in the step 702. In the step 704, the sample of water quality data acquired in the step 702 is wirelessly transmitted to a remote device in wireless communication with a transceiver of the water quality monitoring device. Following the step 704, if the processor is programmed to delay the acquisition of new water quality data (e.g., waiting 10 seconds between new samples to conserve battery power), then the optional condition 705 waits until such delay has elapsed before the method 700 proceeds to the step 702. In other embodiments, the optional condition 705 is omitted and the step 704 proceeds directly to the step 702 once the water quality data has been transmitted. The method 700 is performed, in at least some examples, entirely by one or more processors included in the water quality monitoring device and requires no human intervention.

The water quality monitoring devices described herein and methods of use thereof provide a solution to the long felt but unsolved need of communities needing extensive and updated information on the health of their natural water resources to inform environmental policy, aid conservation efforts, and promote environmental advocacy. Current efforts have come up short and have not resolved the problem. For example, the Environmental Protection Agency (EPA) currently provides the United States' largest source for water quality monitoring data, the Water Quality Portal (WQP), which uses the Water Quality Exchange (WQX) as a tool for user to upload spreadsheets of water quality data. Despite the water quality data being supplied by over 900 federal, state, and tribal agencies, there is still a tremendous lack of updates for current water quality conditions as well as coverage for remote areas. As another example, the California Environmental Protection Agency's Central Coast Region Water Quality website has absolutely zero publicly available graphed water quality data since 2015.

The solution to the problem just described is achieved by providing the efficient and streamlined water quality monitoring devices described herein. The accuracy of each of the sensors of said devices is demonstrated by comparing test data acquired with each of the three sensors to results from a professional multiparameter instrument as a control: the ProDSS Multiparameter Digital Water Quality Meter from YSI (Xylem Analytics). While this particular instrument was used to validate accuracy, it is understood that statements regarding the accuracy of water quality monitoring devices described herein are applicable, in general, to similar devices from various brands, manufacturers, costs, features, and so forth. These types of instruments can cost thousands of dollars, measure far more parameters than are necessary for useful water quality data, require a USB connection to transfer the data, and importantly, require a person to be at the testing location if they want the data to be made available within any reasonable amount of time. Furthermore, such devices often incorporate buttons, displays, touch screens, and other user interfaces which further add to their complexity/difficulty of use and cost to manufacture.

Figure 8:
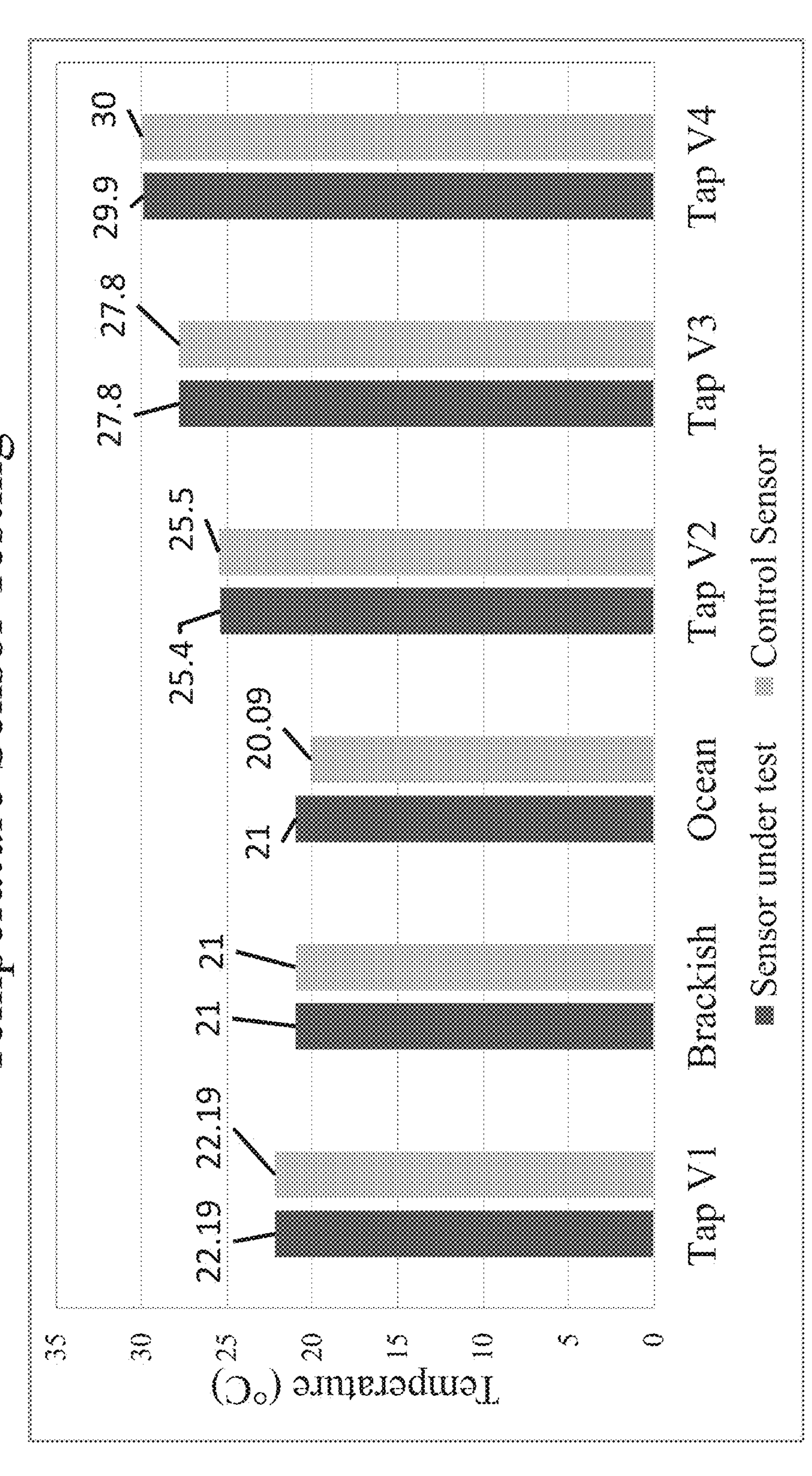
FIG. 8 shows a plot of temperature sensor testing data, in accordance with an embodiment of the present disclosure.

FIG. 8 verifies that the temperature sensors utilized herein are well within the levels of accuracy of more expensive water quality parameter instruments. Six tests were performed for to assess accuracy compared to the control sensor. The first test (Tap V1) provides data for a first temperature of tap water and indicates a 0.00% difference between the sensor under test and the control sensor. The second test (Brackish) provides data for a temperature of a sample of brackish water (i.e., water from a natural environment more salinity than freshwater, but not as much as seawater) and indicates a 0.00% difference between the sensor under test and the control sensor. The third test (Ocean) provides data for a temperature of a sample of ocean water and indicates a 4.53% difference between the sensor under test and the control sensor. The fourth test (Tap V2) provides data for a second temperature of tap water and indicates a 0.39% difference between the sensor under test and the control sensor. The fifth test (Tap V3) provides data for a third temperature of tap water and indicates a 0.00% difference between the sensor under test and the control sensor. The sixth test (Tap V4) provides data for a fourth temperature of tap water and indicates a 0.33% difference between the sensor under test and the control sensor.

Figure 9:
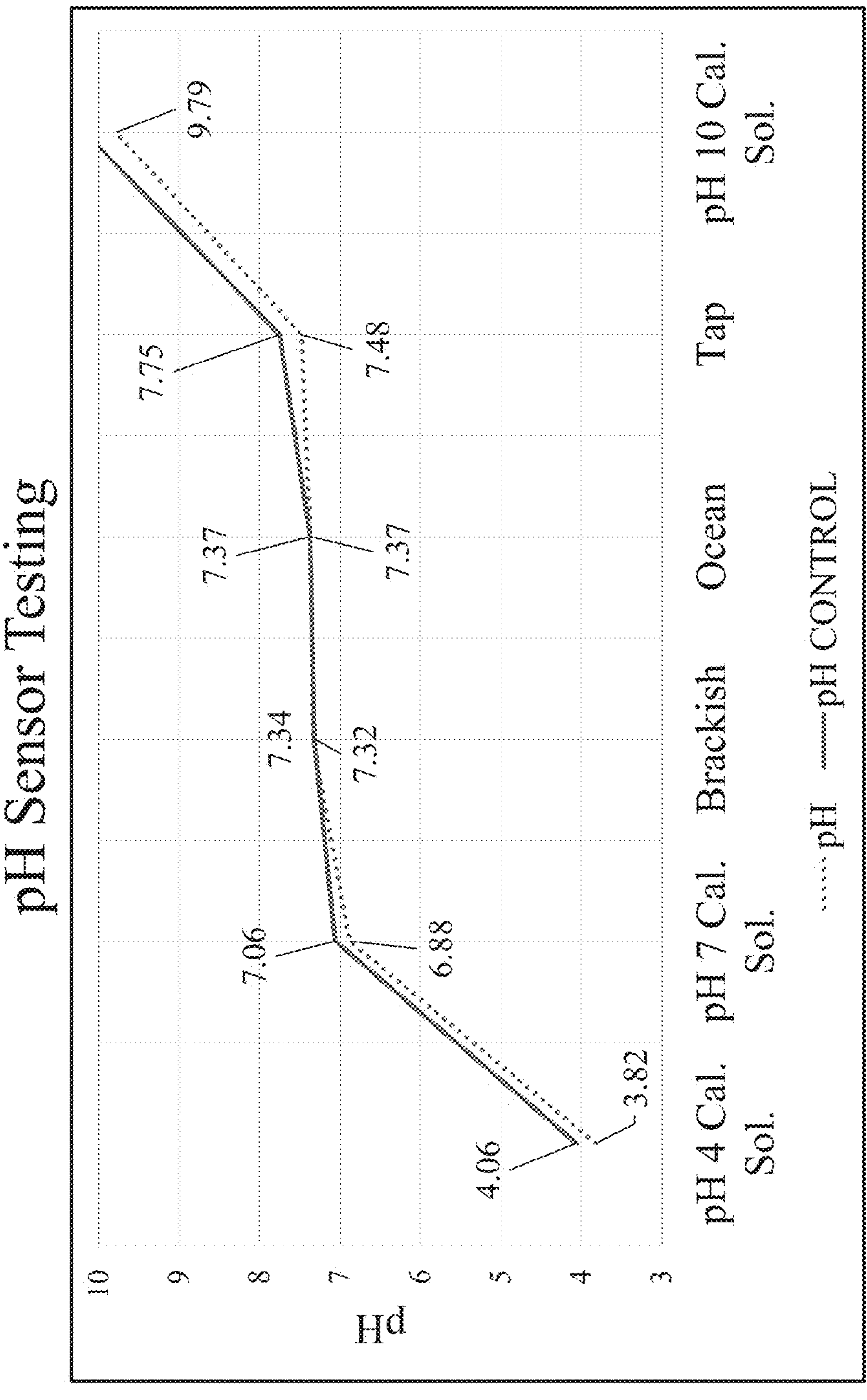
FIG. 9 shows a plot of pH sensor testing data, in accordance with an embodiment of the present disclosure.

FIG. 9 verifies that the pH sensors utilized herein are well within the levels of accuracy of more expensive water quality parameter instruments. Six tests were performed for six solutions of differing pH levels to compare pH data from the sensor under test with the control sensor. The six tests include three calibration solutions of known pH (i.e., 4, 7, and 10) as well as three tests of different local water sources with unknown pH (i.e., brackish, ocean, and tap) to verify performance against the more expensive control sensor. All of the tests besides the test for tap water indicate less than a 3.81% difference with the control sensor, with the tap water test indicating a 6.25% difference and the brackish test indicating the smallest difference at 0.27%.

Figure 10:
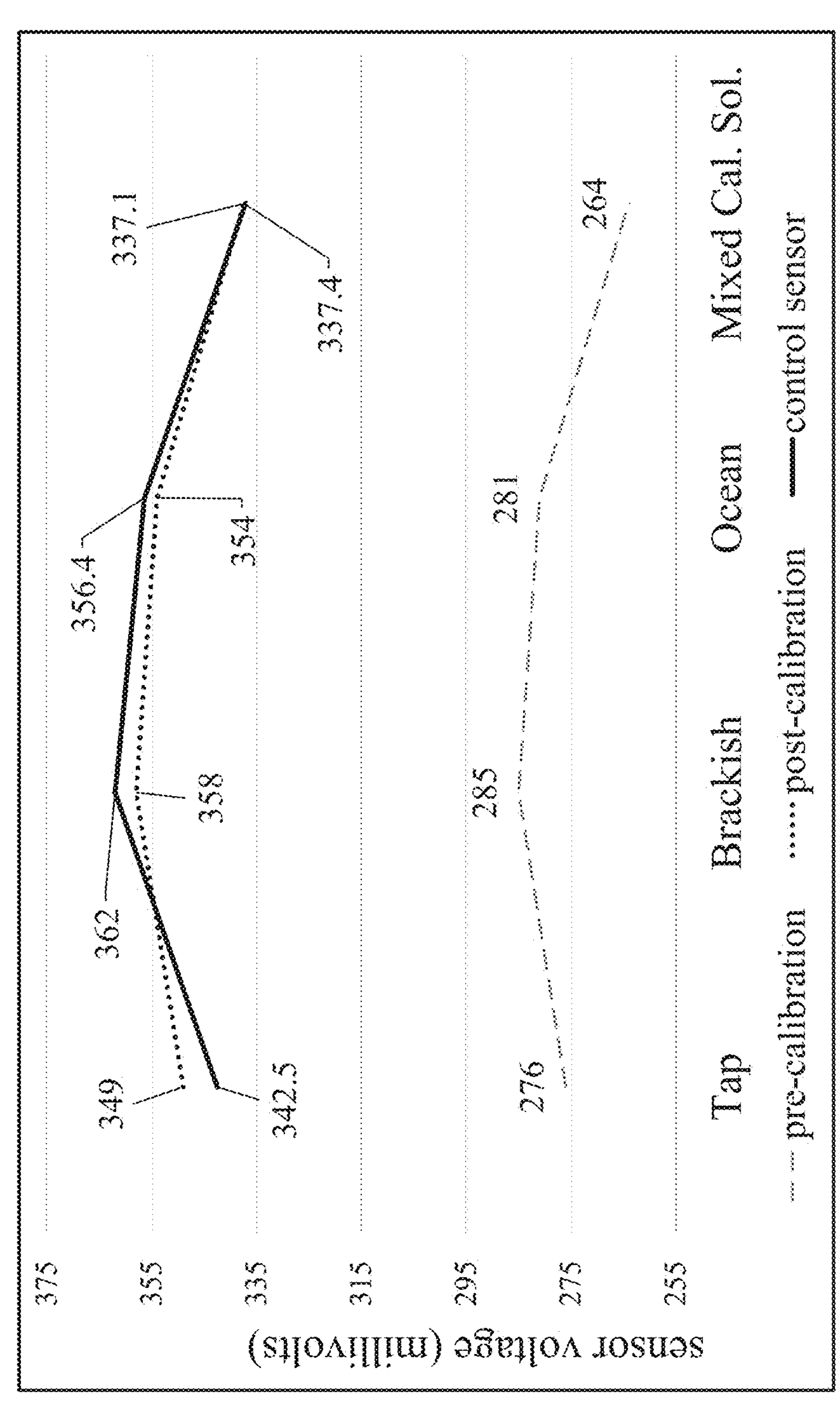
FIG. 10 shows a plot of ORP sensor testing data, in accordance with an embodiment of the present disclosure.

FIG. 10 demonstrates the benefit of calibrating the ORP sensor of each water quality monitoring device as well as how closely the performance matches that of the control sensor. Four tests were performed for four different solutions, including tap water, brackish, and ocean water as used in the pH sensor tests. The fourth test is a mixed calibration solution created by combining two known calibration solutions so as to verify consistency with the more expensive control sensor. Once calibrated, the difference in ORP millivolt readings between the ORP sensor and the control center drastically improved from a roughly 20% difference to roughly a 3% difference. Specifically, the tap water sample showed a difference with the control sensor improving from a 19.42% difference to a 1.90% difference. The brackish sample improved from a 21.27% difference to a 1.10% difference. The ocean sample improved from a 21.16% difference to a 0.67% difference. The mixed calibration solution sample improved from a 21.57% difference to a 0.09% difference.

At this point it should be noted that techniques for creating effective and affordable water quality monitoring devices in accordance with the present disclosure as described above may involve the processing of input data and the generation of output data to some extent. This input data processing and output data generation may be implemented in hardware or software. For example, specific electronic components may be employed in one or more processors, a dedicated circuit or similar or related circuitry for implementing the functions associated with acquiring water quality data, transmitting water quality data, and so forth in accordance with the present disclosure as described above. Alternatively, one or more processors operating in accordance with instructions may implement the functions associated with controllers, algorithms, or other processes in accordance with the present disclosure as described above. If such is the case, it is within the scope of the present disclosure that such instructions may be stored on one or more non-transitory processor readable storage media (e.g., a magnetic disk, SSD or other storage medium), or transmitted to one or more processors via one or more signals embodied in one or more carrier waves.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

The invention claimed is:

1. A water quality monitoring device comprising:

a plurality of sensors configured to acquire water quality data from a sample of a body of water, the water quality data including temperature data, pH data, and ORP data, the plurality of sensors including:

a temperature sensor configured to acquire the temperature data from the body of water, wherein the temperature sensor is calibrated using a first plurality of water samples, the first plurality of water samples including at least samples of brackish water, ocean water, and tap water;

a potential of hydrogen (pH) sensor configured to acquire the pH data from the body of water, wherein the pH sensor is calibrated using a second plurality of water samples including:

a plurality of water samples of known pHs; and at least three water samples of unknown pHs including samples of brackish water, ocean water, and tap water; and an oxidation-reduction potential (ORP) sensor configured to acquire the ORP data from the body of water, wherein the ORP sensor is calibrated using a third plurality of water samples including:

at least one water sample of a known pH; and at least two water samples of unknown pHs including samples of brackish water and ocean water;

a transceiver configured to wirelessly transmit the water quality data over a communication channel to a server;

a memory storing program instructions;

one or more processors configured to execute the program instructions stored in the memory and to:

operate the plurality of sensors to generate the temperature data, the pH data, and the ORP data of the water quality data; and operate the transceiver to wirelessly transmit the water quality data;

a power source configured to provide power to the plurality of sensors, the transceiver, the memory, and the one or more processors; and a housing containing the transceiver, the memory, the one or more processors, and the power source.

2. The water quality monitoring device of claim 1, wherein the memory is configured not to store the water quality data.

3. The water quality monitoring device of claim 1, wherein the device is configured to acquire and wirelessly transmit the water quality data in real time.

4. The water quality monitoring device of claim 1, wherein the one or more processors are further configured to:

operate the plurality of sensors to generate additional water quality data every 10 seconds, the additional water quality data including additional temperature data, additional pH data, and additional ORP data acquired from an additional sample of the body of water, and operate the transceiver to immediately transmit the additional water quality data in response to the plurality of sensors generating the additional water quality data.

5. The water quality monitoring device of claim 1, wherein the one or more processors are further configured to:

operate the transceiver to wirelessly receive additional water quality data from a separate water quality monitor device configured to acquire the additional water quality data from the body of water;

combine the water quality data with the additional water quality data; and operate the transceiver to transmit the combined water quality data over the communication channel to the server.

6. The water quality monitoring device of claim 1, further comprising a renewable power generator coupled to the water quality monitoring device and configured to provide renewable power to the power source, wherein the renewable power generator includes one or more photovoltaic panels, one or more wind turbines, and/or one or more hydroelectric generators.

7. The water quality monitoring device of claim 1, wherein the transceiver is further configured to communicate using a Wi-Fi communication protocol.

8. A water monitoring system comprising:

at least two of the water quality monitoring device of claim 1 including a first water quality monitoring device and a second water quality monitoring device, the first water quality monitoring device configured to acquire first water quality data from a first location in the body of water and transmit the first water quality data over the communication channel to the server, the second water quality monitoring device configured to acquire second water quality data from a second location in the body of water and transmit the second water quality data over the communication channel to the server.

9. The water quality monitoring device of claim 1, wherein the body of water feeds a hydroelectric dam, and wherein the power source is powered by the hydroelectric dam.

10. The water quality monitoring device of claim 1, wherein the plurality of water samples of known pHs of the second plurality of water samples includes samples with pHs of 4, 7, and 10.

11. A method of monitoring a body of water, the method comprising:

providing a water quality monitoring device including:

a plurality of sensors including:

a temperature sensor, wherein the temperature sensor is calibrated using a first plurality of water samples, the first plurality of water samples including at least samples of brackish water, ocean water, and tap water;

a potential of hydrogen (pH) sensor, wherein the pH sensor is calibrated using a second plurality of water samples including:

a plurality of water samples of known pHs; and at least three water samples of unknown pHs including samples of brackish water, ocean water, and tap water; and an oxidation-reduction potential (ORP) sensor, wherein the ORP sensor is calibrated using a third plurality of water samples including:

at least one water sample of a known pH; and at least two water samples of unknown pHs including samples of brackish water and ocean water;

a transceiver;

a memory storing program instructions;

one or more processors configured to execute the program instructions stored in the memory;

a power source; and a housing containing the transceiver, the memory, the one or more processors, and the power source;

establishing, by the one or more processors, a communication channel between the transceiver and a server;

submerging the temperature sensor, the pH sensor, and the ORP sensor into the body of water;

operating, by the one or more processors, the plurality of sensors to acquire water quality data from a sample of the body of water, the water quality data including temperature data acquired with the temperature sensor, pH data acquired with the pH sensor, and ORP data acquired with the ORP sensor; and operating, by the one or more processors, the transceiver to wirelessly transmit the water quality data over the communication channel to the server.

12. The method of claim 11, wherein the memory is programmed not to store the water quality data.

13. The method of claim 11, further comprising acquiring and wirelessly transmitting the water quality data in real time.

14. The method of claim 11, further comprising:

generating additional water quality data every 10 seconds, the additional water quality data including additional temperature data, additional pH data, and additional ORP data acquired from an additional sample of the body of water; and immediately transmitting the additional water quality data in response to the plurality of sensors generating the additional water quality data.

15. The method of claim 11 further comprising:

wirelessly receiving additional water quality data from a separate water quality monitor device configured to acquire the additional water quality data from the body of water;

combining the water quality data with the additional water quality data; and transmitting the combined water quality data over the communication channel to the server.

16. The method of claim 11 wherein the wireless protocol is a Wi-Fi communication protocol.

17. The method of claim 11, further comprising:

providing at least two of a water quality monitoring device including a first water quality monitoring device and a second water quality monitoring device, the first water quality monitoring device acquiring first water quality data from a first location in the body of water and transmitting the first water quality data over the communication channel to the server, the second water quality monitoring device acquiring second water quality data from a second location in the body of water and transmitting the second water quality data over the communication channel to the server.

18. The method of claim 11 wherein establishing the communication channel between the transceiver and the server comprises the server hosting a publicly accessible website that displays the temperature data, the pH data, and the ORP data in real time.

19. The method of claim 11, wherein the body of water feeds a hydroelectric dam, and wherein the power source is powered by the hydroelectric dam.

20. The method of claim 11, wherein the plurality of water samples of known pHs of the second plurality of water samples includes samples with pHs of 4, 7, and 10.

* * * * *